(12) United States Patent
Zborowski et al.

(10) Patent No.: US 6,467,630 B1
(45) Date of Patent: Oct. 22, 2002

(54) CONTINUOUS PARTICLE AND MOLECULE SEPARATION WITH AN ANNULAR FLOW CHANNEL

(75) Inventors: Maciej Zborowski, Bay Village; Jeff Chalmers, Columbus; Lee R. Moore, Sasamore Hills, all of OH (US)

(73) Assignees: The Cleveland Clinic Foundation, Cleveland, OH (US); The Ohio State University, Columbus, OH (US)

( * ) Notice: Subject to any disclaimer, the term of this patent is extended or adjusted under 35 U.S.C. 154(b) by 0 days.

(21) Appl. No.: 09/653,432

(22) Filed: Sep. 1, 2000

Related U.S. Application Data

(60) Provisional application No. 60/152,303, filed on Sep. 3, 1999.

(51) Int. Cl.[7] .............................. B03B 5/60; B03C 5/02
(52) U.S. Cl. ...................................................... 209/459
(58) Field of Search ............................. 209/127.4, 128, 209/129, 130, 131, 127.1

(56) References Cited

U.S. PATENT DOCUMENTS

| | | | |
|---|---|---|---|
| 2,056,426 A | 10/1936 | Frantz | 209/232 |
| 3,608,718 A | 9/1971 | Aubrey, Jr. et al. | 209/214 |
| 3,839,201 A | 10/1974 | Miller | 210/22 |

(List continued on next page.)

FOREIGN PATENT DOCUMENTS

| | | | |
|---|---|---|---|
| DE | 3827252 | 2/1990 | B03C/1/30 |
| DE | 19860117 | 7/2000 | B01D/57/02 |
| EP | 0289858 A1 | 11/1988 | B01D/46/24 |
| GB | 2319191 A | 5/1998 | B10D/49/00 |

OTHER PUBLICATIONS

Derwent Publications Ltd., English Abstract of SU 1714 480A, titled "Electrophoretic separation device of biological and non–biological objects–has sepn. chamber formed by two coaxially positioned cylinders and uses through axial holes in cylinders to pass cooling fluid".

(List continued on next page.)

*Primary Examiner*—Donald P. Walsh
*Assistant Examiner*—Mark J. Beauchaine
(74) *Attorney, Agent, or Firm*—Nenad Pejic; Calfee, Halter & Griswold LLP

(57) ABSTRACT

The present invention provides apparatuses and methods for continuously separating particles of interest from a heterogeneous particle population. The heterogeneity can be based on, for example, magnetic susceptibility, particle size, thermal diffusion, phase solubility, and combinations of the preceding. Based on the heterogeneity, a separation force capable of exploiting the separand (i.e., particles subject to the separation process) is provided. The various embodiments of the present invention preferably employ an annular separation channel, appropriate separation force and flow compartments. In a first embodiment, an annular separation channel having semi-permeable inner and outer cylindrical walls is used to generate lateral convection forces. In a second embodiment of the present invention, an annular separation channel having heat conductive inner and outer cylindrical walls is used to generate thermal diffusion forces. In a third embodiment, an annular separation channel having non-permeable inner and outer cylindrical walls is used to generate a solubility difference separation force based on solubility coefficient differences between phases of flow compartments. In a fourth embodiment, an annular separation channel having electrically conductive inner and outer cylindrical walls is used to generate an electrophoretic separation force. In a fifth embodiment, an annular separation channel having electrically conductive inner and outer cylindrical walls is used to generate a dielectrophoretic separation force. Yet other embodiments of the present invention provide for the combination of separation forces including lateral convection, thermal diffusion, solubility difference, electrophoretic, dielectrophoretic, and magnetic separation forces.

10 Claims, 3 Drawing Sheets

U.S. PATENT DOCUMENTS

| | | | |
|---|---|---|---|
| 4,136,950 A | | 1/1979 | Labrum et al. ............... 356/28 |
| 4,260,394 A | * | 4/1981 | Rich .......................... 201/17 |
| 4,454,016 A | | 6/1984 | Rabinowitz et al. ........ 204/308 |
| 4,594,149 A | | 6/1986 | Andres et al. ................. 209/1 |
| 4,618,409 A | * | 10/1986 | Lovegrove .................. 204/272 |
| 4,663,029 A | | 5/1987 | Kelland et al. ............. 209/214 |
| 4,683,042 A | * | 7/1987 | Scott .......................... 204/272 |
| 4,976,866 A | | 12/1990 | Grinstead et al. ........... 210/638 |
| 5,039,426 A | | 8/1991 | Giddings .................... 210/695 |
| 5,047,154 A | | 9/1991 | Comstock et al. .......... 210/636 |
| 5,049,540 A | | 9/1991 | Park et al. ..................... 505/1 |
| 5,053,344 A | | 10/1991 | Zborowski et al. ......... 436/177 |
| 5,106,468 A | | 4/1992 | Chimenti ................. 204/180.1 |
| 5,169,006 A | | 12/1992 | Stelzer .................... 209/223.1 |
| 5,180,921 A | | 1/1993 | Moreau et al. ............. 250/554 |
| 5,224,604 A | | 7/1993 | Duczmal et al. ............. 209/12 |
| 5,465,849 A | | 11/1995 | Wada et al. ................ 209/214 |
| 5,536,475 A | | 7/1996 | Moubayed et al. ......... 422/101 |
| 5,541,072 A | | 7/1996 | Wang et al. ............... 435/7.21 |
| 5,568,869 A | | 10/1996 | Turkenich et al. .......... 209/212 |
| 5,641,919 A | | 6/1997 | Dahneke .................... 73/865.5 |

OTHER PUBLICATIONS

Derwent Publications Ltd., English Abstract of SU 744 285A, titled "Dielectric–phoretic separation of dispersed suspended particles—by using central and outer electrode in ultrasonic vibration field connected to synchronised supply".

Derwent Publications Ltd., English Abstract of DD 213 360A, titled "Dielectrophoretic collection of suspended particles—by applying homogeneous electric high frequency field".

Journal of Magnetism and Magnetic Materials 122(1993) 367–370. North–Holland. "Single Cell Magnetophoresis and its Diagnostic Value", Chirov, et al.

Christian–Albrechts–University of Kiel, Magnetocytometer for Biological Applications. (3 pages) Undated.

Analytical Cell Magnetophoresis, V. Chikov, a. Kuznetsov and W. Schutt, Institute of Chemical Physics Moscow and Department of Internal Medicine, University Rostock. pp. 381–388. Undated.

"Magnetophoresis: I. Detection of Magnetically Labeled Cells", S. Winoto–Morbach, V. Tchikov, and W. Muller–Ruchholtz, Journal of Clinical Laboratory Analysis 8:400–406 (1984).

"Magnetophoresi: II. Quantification of Iron and Hemoglobin Content at the Single Erthyrocyte Level", S. Winoto–Morbach, V. Tchikov, and W. Muller–Ruchholtz, Journal of Clinical Laboratory Analysis 9:42–46 (1995).

"Magnetocytometry for Detecting Cell Labeling with Magnetic Immunomicrosphers", V. Tchikov, s. Winoto–Morbach, W. Muller–Rechholtz, pp. 176–184, Undated.

"Biomedical and clinical applications of automated single cell electrophoresis", VCH Verlagsgesellscnatt mbH. D–6940 Weinheim, 1990. (6 Pages), Undated.

"Electrophoretic Fingerprinting and the Biological Activity of Colloidal Indicators", B. J. Marlow and D. Fairhurst, Mar. 9, 1988, Langmuir. (5 pages).

"Cell Electrophoresis: Proceedings of the International Meeting, Rostock, German Democratic Republic, Sep. 24–28, 1984", Walter de Gruyt, New York 1985. (8 pages).

"Magnetophoretic Techniques", Moscow Rostock 1985. (3 pages).

"Determination of the Magnetic Susceptibility of Labeled Particles By Video Imaging", Chemical Engineering Science, vol. 51, No. 6, pp. 947–956. 1996. Reddy et al.

"Quantative Analysis of Leukocyte Membrane Antigen Expression: Normal Adult Values", Cytometry (Communications in Clinical Cytometry) 26:137–147 (1996). Bikoue et al.

"Application of Magnetic Susceptibility Gradients to Magnetic Separation", American Institute of Physics. 1984. pp. 2592–2594. Hwang et. al.

"Observations of Particle Trajectories Near a Magnetized Fiber", United States Department of Energy, Morgantown Energy Technology Center, Sep. 1978. (35 pages). Treat et al.

"High gradient magnetic separation of cells on the basis of expression levels of cell surface antigens" by Thomas, et al., *J. of Immunological Methods*, 154 (1992), pp. 245–252.

"Magnetic Flow sorting using a model system of human Lymphocytes and a colloidal magnetic label", By Zborowski, et al., *Am. Soc. For Artificial Int. Organs*, May 1996; 42:pp.M666–M671.

"Study of colloidal magnetite–binding erythrocytes: Prospects for cell separation" by Plavins et al., *J. Magnetism and magnetic Materials*, (1993) 122: 349–353.

* cited by examiner

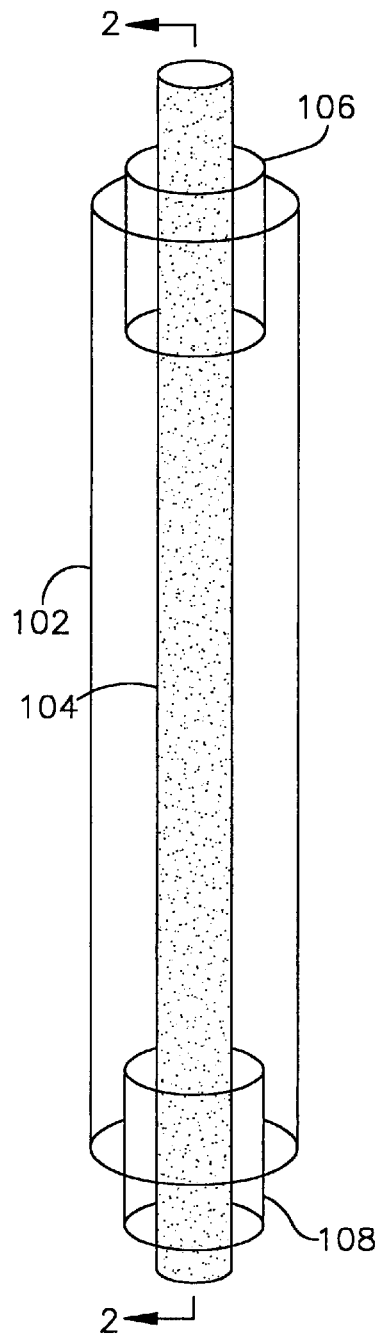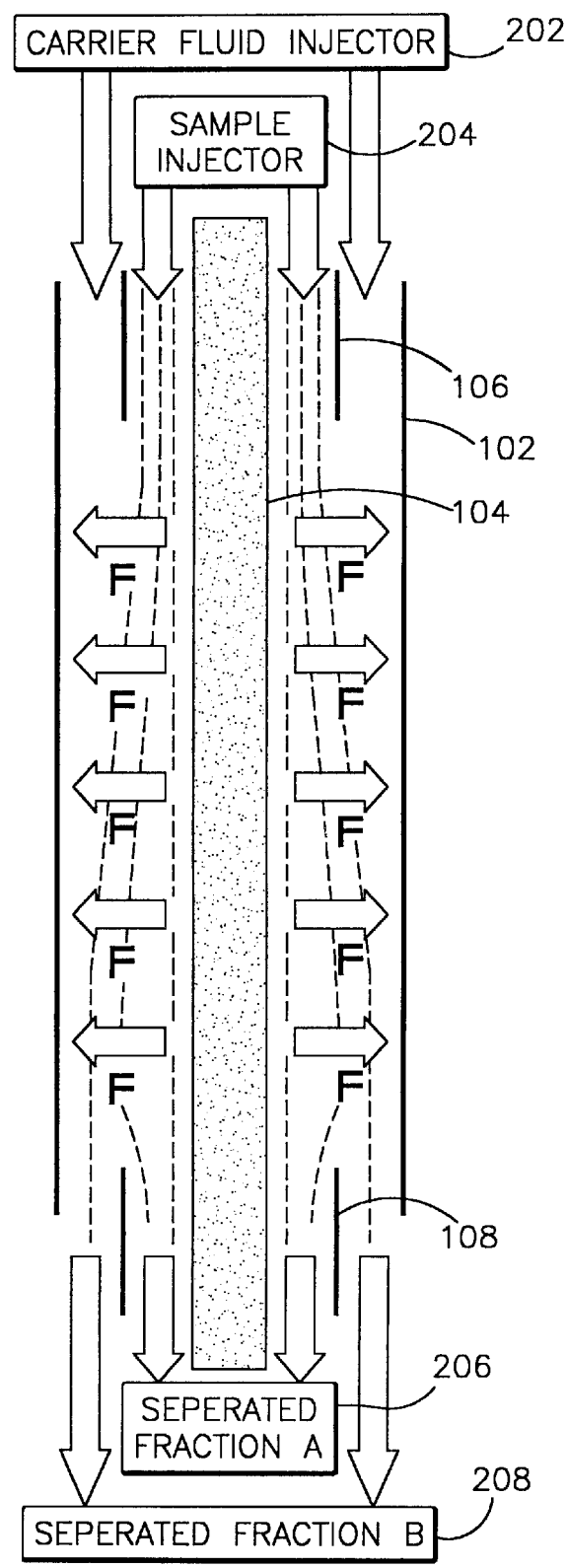
Fig.1
Fig.2

CONTINUOUS PARTICLE AND MOLECULE SEPARATION WITH AN ANNULAR FLOW CHANNEL

This application claims the benefit of U.S. Provisional Application(s) No(s). 60/152,203 filing date Sep. 3, 1999.

FIELD OF THE INVENTION

The invention relates generally to a device and method for continuously sorting particles and, more particularly, to a device and method for sorting particles through the use of an annular flow chamber and one or more types of separation forces.

BACKGROUND OF THE INVENTION

Generally, particle separation devices separate particle populations of interest from a suspension and/or other types of particles. The principal method of operation of early particle separation devices relied on a particle's physical parameters to distinguish that particle from a suspension and/or other types of particles. Examples of these bulk separation techniques include filtration, which is based on particle size, and centrifugation, which is based on particle density. These techniques are effective as long as the particle population of interest is significantly different, with respect to size or density, from the suspension and/or the other particles in the population.

As a subset of bulk separating, continuous separation techniques also exist. The continuous separation of particles in flowing solution requires a well-defined and well-controlled fluid flow pattern. Typically, continuous particle separation devices employ rectangular separation channels. The rectangular geometry of such separation channels results in several advantages including, for example, ease of manufacture, ease of control of fluid flows inside the channels, and ease of design and implementation of forces that drive the separation.

However, rectangular separation channels also suffer from a drawback known as the sidewall effect. The sidewall effect distorts the fluid flow pattern at the side walls of the rectangular separation channel and, hence, adversely affects the performance of the sorting device such as, for example, its resolving power. Hence, it is highly desirable to provide methods and devices for separating particles that do not suffer from sidewall effects and can employ any one of a diverse number of separation forces.

SUMMARY OF THE INVENTION

The present invention is particularly directed to continuous particle and molecule separation in flowing solutions. More particularly, the present invention addresses the issue of the sidewall effect by wrapping a separation channel around a cylinder running the length of the channel and by joining the sides of the channel to thereby eliminate any side walls. So configured, the separation channel has an annular cross-section that is enclosed by two coaxial cylinders. Such a transformation leaves the length of the separation channel unchanged with the width of the channel laid on the cylinder. The separation channel width is equal to the difference between the radii of the two cylinder walls bounding the separation channel.

In addition, the present invention generates axially-symmetric separation forces that are coaxial with the annular separation channel to continuously separate particles of interest from a heterogeneous particle population. The heterogeneity can be based on, for example, magnetic susceptibility, particle size, thermal diffusion, phase solubility, and combinations of the preceding. Based on the heterogeneity, a separation force capable of interacting with the separand (i.e., particles subject to the separation process) is provided. The particles or separands can be non-organic (e.g., metals) or organic (e.g. cells, viruses, and molecules including proteins and DNA). The various embodiments of the present invention preferably employ an annular separation channel, an appropriate separation force, and flow compartments. In a first embodiment, an annular separation channel having semi-permeable inner and outer cylindrical walls is used to generate lateral convection forces. In a second embodiment of the present invention, an annular separation channel having heat conductive inner and outer cylindrical walls is used to generate thermal diffusion forces. In a third embodiment, an annular separation channel having non-permeable inner and outer cylindrical walls is used to generate a solubility difference separation force based on solubility coefficient differences between phases of flow compartments. In a fourth embodiment, an annular separation channel having electrically conductive inner and outer cylindrical walls is used to generate an electrophoretic separation force. In a fifth embodiment, an annular separation channel having electrically conductive inner and outer cylindrical walls is used to generate a dielectrophoretic separation force. Yet other embodiments of the present invention provide for the combination of separation forces including lateral convection, thermal diffusion, solubility difference, electrophoretic, dielectrophoretic, and magnetic separation forces.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

FIG. 1 is a schematic view of the annular separation channel of the present invention.

FIG. 2 is a longitudinal section of the annular separation channel of the present invention along section lines 2—2 of FIG. 1 and additionally showing carrier and sample injectors and separated fraction outputs

DETAILED DESCRIPTION OF ILLUSTRATED EMBODIMENT

Figure 3:
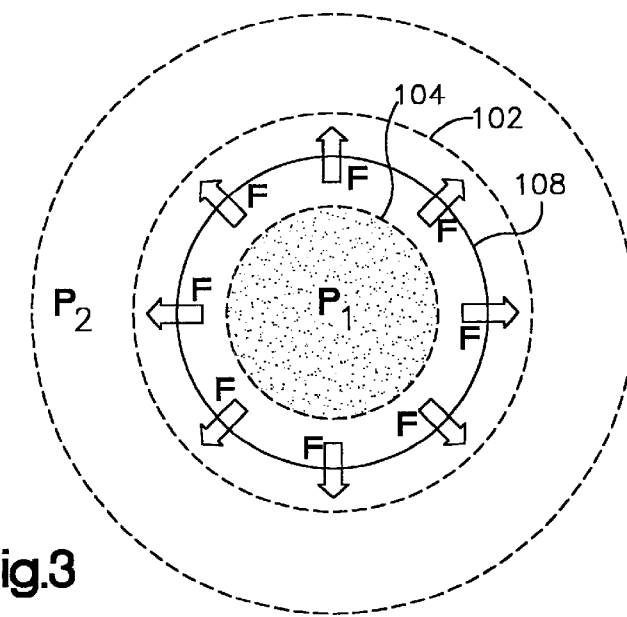
FIG. 3 is a cross-sectional view of an embodiment of the annular separation channel of FIG. 1 illustrating lateral convective separation.

Referring now to FIG. 1, a schematic view of the annular separation channel 100 is shown. The channel 100 has an outer cylindrical wall 102 (sometimes referred to as an "accumulation wall"), an inner cylindrical wall 104, and first and second cylindrical flow splitters 106 and 108, respectively. While two flow splitters are shown, there may be more flow splitters per channel than two.

So configured, the distribution of the flow rates between the carrier fluid injector 202, sample injector 204, separated fraction a 206, and separated fraction b 208, generate flow compartments that are used to divide the separand flow into individual flow compartments. The physical position of the flow compartments can then be adjusted by varying any one or more of the flow splitter location (i.e., radius) in the annular separation channel, and carrier medium and sample flow rates. The distribution of the separation forces (i.e., magnitude and direction) across the cross-section of the annular channel 100, together with the position of the flow compartments, determine the results of the separation. Flow compartments are more fully described in U.S. Pat. No. 5,968,820 to Zborowski et al. titled "Method for Magnetically Separating Cells into Fractionated Flow Streams" (hereinafter Zborowski), which is hereby fully incorporated by reference.

Illustrated in FIG. 2 is a longitudinal section of the annular separation channel 100, along with a schematic representation of carrier fluid injectors 202, sample fluid injector 204, and separated fractions "a" 206 and "b" 208. FIG. 2 also illustrates a preferred system arrangement of the present invention for continuously separating particles with the various embodiments of the annular separation channel disclosed herein. Except as specifically noted in the embodiments to follow, the carrier fluid or medium is preferably phosphate-buffered saline at a physiological concentration of 0.15 mole per liter or other similar medium. Sample injector 204 introduces separands or particles preferably suspended in the same or similar fluid as the carrier medium. As will be presently described, a feature of the present invention is the development and use of radially directed forces "F," which may take the form of any one of a number of identities.

Referring now to FIGS. 2 and 3, an embodiment of the present invention employing a lateral convective force "F" is shown. The convective force "F" is generated by making the outer and inner cylindrical walls 102 and 104, respectively, from a semi-permeable membrane material which allows for the transfer of a carrier medium (i.e., solvent) but not the particles to be separated (i.e., separands). The semi-permeable membrane is preferably made of regenerated or modified cellulose, polyacrylonitrile, polysulfone or polycarbonate. The lateral transport of the carrier medium is driven by a pressure difference of P2− P1 between the inside of the semi-permeable inner wall 104, which is filled with the carrier medium, and the outside of the semi-permeable outer wall 102, which is also filled with the carrier medium. Hence, the carrier medium or fluid is injected inside of the semi-permeable inner wall 104 to form a first pressure P1 and outside of the semi-permeable outer wall 102 to form a second pressure P2, wherein first pressure P1 is greater than second pressure P2. The sample of separands or particle is introduced near the inner wall 104, s shown in FIG. 2. The radial flow of the carrier medium pushes the particles against the semi-permeable outer wall 102 and the resulting radial concentration causes a diffusive flux back towards the center (i.e., towards semi-permeable inner wall 104.) At equilibrium, larger particles stay close to the outer cylindrical wall 102 and are eluted in fraction "b" 208, whereas smaller particles stay farther away from the accumulation wall (i.e., outer wall 102) and are eluted as the fraction "a", 206. It should also be noted that a reverse radial convective transport force can be generated by providing a first pressure P1 that is less than the second pressure P2.

Figure 4:
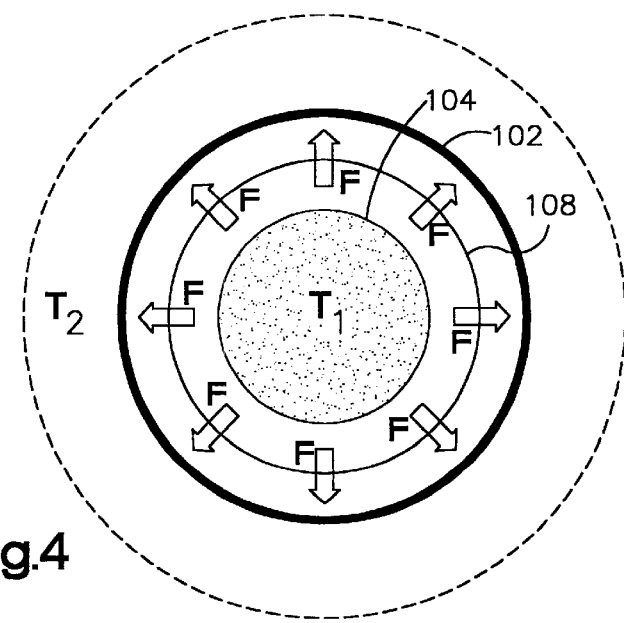
FIG. 4 is a cross-sectional view of an embodiment of the annular separation channel of FIG. 1 illustrating thermal diffusion separation.

Referring now to FIGS. 2 and 4, an embodiment of the present invention employing a thermal diffusion force "F" is shown. In this embodiment, the outer cylindrical wall 102 is made of a heat-conductive material in contact with a large capacity heat reservoir of temperature T2. The inner cylindrical wall 104 is made of a heat-conductive material in contact with a large-capacity heat reservoir of temperature T1. Suitable heat conductive materials include, for example, a copper rod with imbedded heating elements for the heat source T1 (or T2), and a copper cylinder with imbedded cooling elements for the heat sink T2 (or T1, correspondingly). Sample injector 204 introduces separands or particles near the inner cylindrical wall 104 and carrier medium injector 202 introduces a carrier medium into the flow channel. A large temperature difference, T2−T1, drives a thermal diffusion of particles along the radial direction shown. Particles that are characterized by a large thermal diffusion coefficient (such as, for example, certain polymers) are particularly affected. Polymers differing in their thermal diffusion coefficients are collected in different fractions "a" 206 and "b" 208 at the exit from the annular channel. If temperature T1 is less than temperature T2, particles with a large thermal diffusion coefficient tend to be collected in fraction "b" 208 and particles with lesser or no thermal diffusion coefficient tend to be collected in fraction "a" 206.

Figures 5, 6:
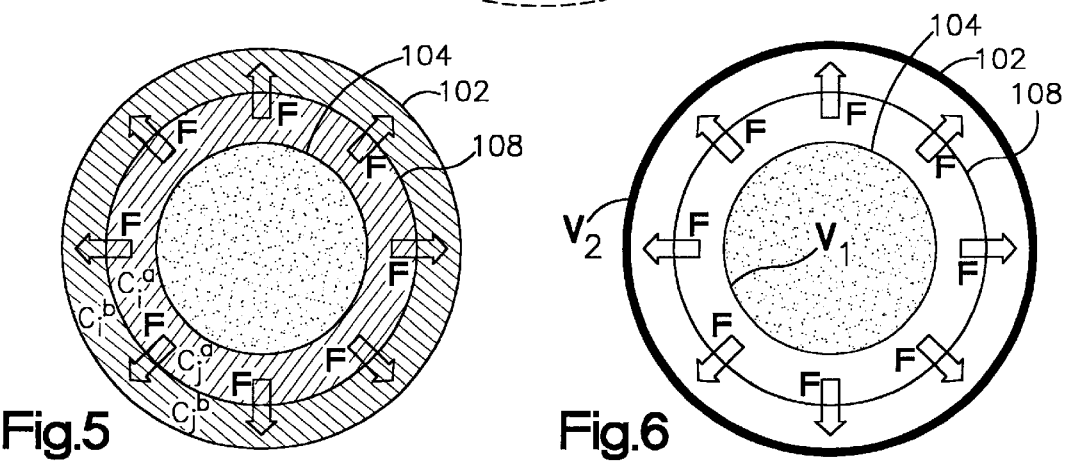
FIG. 5 is a cross-sectional view of an embodiment of the annular separation channel of FIG. 1 illustrating solubility difference separation.
FIG. 6 is a cross-sectional view of an embodiment of the annular separation channel of FIG. 1 suitable for electrophoretic separation and dielectrophoretic separation.

Referring now to FIGS. 2 and 5, an embodiment of the present invention employing a phase separation force "F" is shown. In this embodiment, a thin annular channel facilitates continuous liquid-to-liquid extraction processes in which separands separate between two different liquid phases based on differences in the separands' solubility coefficients. One embodiment of a phase separation force is generated by the solubility difference between an aqueous phase and an organic phase of a mixture of polar and non-polar separands. The polar separands stay in the aqueous phase and the non-polar separands move to the organic phase. Such a partition is generated by introducing an organic solvent as a carrier medium 202 and a mixture of separands "$C_i$" (non-polar) and "$C_j$" (polar) in an aqueous solvent as the sample 204. Suitable organic solvents include ether and hexane. Providing that there is no mixing between the two flows (i.e., the flow is substantially laminar), and the flow rates are chosen so that the residence time inside the separation channel 100 is significantly longer than the diffusion time necessary for the separands to traverse the channel width, the organic phase becomes enriched with the non-polar separand "$C_i$," with the final concentration of non-polar separands in the organic phase being "$C_i^b$." The aqueous phase becomes enriched with the polar separand "$C_j$," with the final concentration of polar separands in the aqueous phase being "$C_j^a$." Assuming that the concentration of the non-polar separand remaining in the aqueous phase is "$C_i^a$" and that the concentration of the polar separand in the organic phase is "$C_j^b$," a separation factor a can be characterized as follows:

$$\alpha = \left( \frac{C_i^b / C_i^a}{C_j^b / C_j^a} \right)$$

The embodiments of FIGS. 1 through 5 may also be combined individually, collectively, or otherwise combinatorially with magnetic particle separation methods. More specifically, the lateral convective separation illustrated in FIGS. 2 and 3 can be combined with the magnetic separation methods and apparatus described in Zborowski, which is hereby fully incorporated by reference. Zborowski describes, among other things, the use of an annular separation channel in combination with magnetic forces and flow compartments to achieve particle separation. The thermal diffusion separation illustrated in FIGS. 2 and 4 and the solubility difference separation illustrated in FIGS. 2 and 5 can also be combined with the magnetic separation described in Zborowski.

Figure 7:
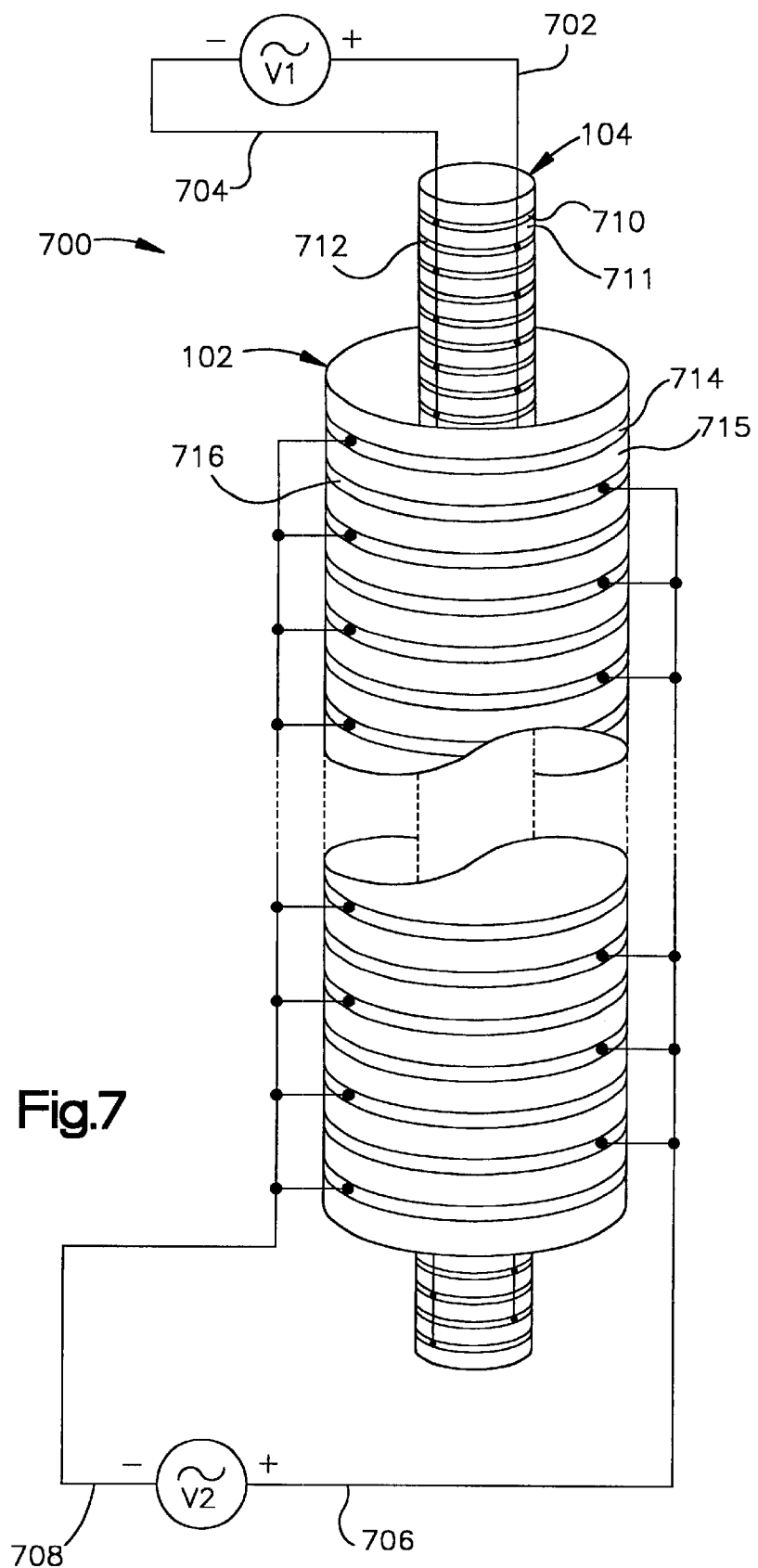
FIG. 7 illustrates another embodiment of the present invention suitable for dielectrophoretic separation.

Referring now to FIGS. 2 and 6, an embodiment of the present invention employing either an electrophoretic or dielectrophoretic separation force "F" is shown. In this embodiment, the outer cylindrical wall 102 is made of an electrically conductive material at an electric potential of V2 volts. The inner cylindrical wall 104 is made of an electrically conductive material at an electric potential of V1 volts. Suitable electrically conductive materials include copper, steel, or metal alloy typically used for electrode construction. The electrically conductive material may be separated by an insulator to form a pattern on cylindrical walls 102 and 104 as shown in FIG. 7. Examples of geometrical patterns used for electrode construction include interdigitated electrodes for dielectrophoresis. Sample injector 204 introduces separands or particles near the inner cylindrical wall 104 and carrier medium injector 202 introduces a carrier medium into the flow channel. An electric potential difference, V2−V1, drives an electrically susceptible particles along the radial direction shown. This effect is known as electrophoretic mobility. Particles that are characterized by a large electrophoretic mobility are particularly affected. Particles differing in their electrophoretic mobility are collected in different fractions "a" 206 and "b" 208 at the exit from the annular channel. If electrical potential V1 is less than electrical potential V2, particles with large electrophoretic mobility tend to be collected in fraction "b" 208 and particles with lesser or no electrophoretic mobility factors tend to be collected in fraction "a" 206.

FIGS. 2 and 6 are also applicable to dielectrophoretic separation forces. The difference between electrophoretic separation and dielectrophoretic separation being that a varying electric field is used in dielectrophoretic separation, whereas a static electric field is used for electrophoretic separation. Therefore, the above discussion of electrophoretic separation is equally applicable to dielectrophoretic separation with the exception of the varying electric fields as represented by varying potentials V1 and V2.

Referring now to FIG. 7, a separation channel 700 particularly suitable for dielectrophoresis is shown. The channel 700 includes a plurality of electrodes on outer cylindrical wall 102 such as, for example, electrodes 714 and 716, and inner cylindrical wall 104 such as, for example, electrodes 710 and 712. An insulator 715 resides between electrodes 714 and 716. Similarly, an insulator 711 resides between electrodes 710 and 712. The electrodes and insulators are preferably interdigitated as shown in FIG. 7 with equal distances between the electrodes. However, the distances may also be non-equally spaced to either concentrate or dilute the generated electrical forces.

A first source providing varying electrical potential V1 is in circuit communication with the inner cylindrical wall 104 electrodes. More specifically, positive terminal 702 and negative terminal 704 provide each pair of electrodes such as, for example, electrodes 712 and 710, respectively, with the varying electrical potential V1. This configuration of electrode connection is continued through the entire inner cylindrical wall 104 electrodes with the electrode next to electrode 712 being connected to the opposite terminal. In this manner, each pair of electrodes are of opposite polarity and have an insulator therebetween. A second source providing varying electrical potential V2 is in circuit communication with the outer cylindrical wall 102 electrodes. In particular, positive terminal 706 and negative terminal 708 provide each pair of electrodes such as, for example, electrodes 716 and 714, respectively, with the varying electrical potential V2. This configuration of electrode connection is also continued through the entire outer cylindrical wall 102 electrodes with the electrode next to electrode 716 being connected to the opposite terminal. In this manner, each pair of electrodes are of opposite polarity and have an insulator therebetween.

Additional advantages and modifications will readily appear to those skilled in the art. For example, the sorting methods and apparatuses of the present invention may also be applied to particles other than cells, such as cell organelles, viruses, inorganic particles, such as soil particles, and molecules such as proteins and DNA. The distribution of particles between sorted fractions can be controlled by adjusting the properties of the carrier medium and/or the separation forces. For example, increasing or decreasing the flow rate of the carrier medium decreases or increases the amount of time a separand is within the annular separation channel. Changing the magnitude of the separation force or the distribution of magnitude of the separation force between the inner and outer cylindrical walls of the annular separation channel changes the distribution of particles between sorted fractions. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. A method of separating particles comprising the steps of:
   (a) generating a first varying electrical potential;
   (b) generating a second varying electrical potential;
   (c) continuously introducing a plurality of particles into a space between the first varying electrical potential and the second varying electrical potential;
   (d) subjecting the particles to a radial electrophoretic force causing at least some of the particles to undergo radial displacement; and
   (e) continuously recovering at least a portion of the particles.

2. A method for separating particles comprising the steps of:
   (a) generating an organic liquid phase flow;
   (b) generating an aqueous liquid phase flow;
   (c) continuously introducing a mixture of polar and non-polar particles into the aqueous liquid phase flow thereby causing at least a portion of the non-polar particles to move from the aqueous liquid phase flow to the organic liquid phase flow; and
   (d) continuously recovering at least a fraction of the polar and non-polar particles from the organic liquid phase flow and the aqueous liquid phase flow.

3. A channel for separating particles comprising:
   (a) a first cylindrical wall having a first radius;
   (b) a first plurality of electrodes interdigitated along at least a portion of the first cylindrical wall;
   (c) a second cylindrical wall having a second radius, the second radius being greater than the first radius;

(d) a second plurality of electrodes interdigitated along at least a portion of the second cylindrical wall; and (e) a space between the first and second cylindrical walls configured to allow development of a dielectrophoretic force.

4. The channel of claim 3 wherein the first plurality of electrodes comprises a plurality of electrodes each configured circumferentially on the inner cylindrical wall.

5. The channel of claim 3 wherein the second plurality of electrodes comprises a plurality of electrodes each configured circumferentially on the outer cylindrical wall.

6. A channel for separating particles comprising:

a first cylindrical portion comprising:
a first radius; and
a first pattern of first electrodes; and a second cylindrical portion comprising:
a second radius different from the first radius; and
a second pattern of second electrodes.

7. The channel of claim 6 wherein the first pattern of first electrodes comprises a plurality of electrodes separated by a plurality of insulators.

8. The channel of claim 6 wherein the second pattern of second electrodes comprises a plurality of electrodes separated by a plurality of insulators.

9. The channel of claim 6 wherein the first pattern of electrodes comprises a plurality of annular electrodes.

10. The channel of claim 6 wherein the second pattern of electrodes comprises a plurality of annular electrodes.

* * * * *

UNITED STATES PATENT AND TRADEMARK OFFICE
CERTIFICATE OF CORRECTION

PATENT NO.    : 6,467,630 B1
DATED         : October 22, 2002
INVENTOR(S)   : Zborowski et al.

It is certified that error appears in the above-identified patent and that said Letters Patent is hereby corrected as shown below:

<u>Title page,</u>
Item [75], Inventors, please delete the word "Sasamore" and insert -- Sagamore --.

Signed and Sealed this

Eighteenth Day of February, 2003

JAMES E. ROGAN
*Director of the United States Patent and Trademark Office*